(12) United States Patent
Rosenthal et al.

(10) Patent No.: US 6,281,501 B1
(45) Date of Patent: Aug. 28, 2001

(54) MULTIPLE GAIN PORTABLE NEAR-INFRARED ANALYZER

(75) Inventors: Todd C. Rosenthal, Hagerstown; Stuart W. Wrenn, Frederick, both of MD (US)

(73) Assignee: Zeltex, Inc., Hagerstown, MD (US)

( * ) Notice: Subject to any disclaimer, the term of this patent is extended or adjusted under 35 U.S.C. 154(b) by 0 days.

(21) Appl. No.: 09/061,893

(22) Filed: Apr. 17, 1998

Related U.S. Application Data

(60) Provisional application No. 60/044,703, filed on Apr. 18, 1997.

(51) Int. Cl.[7] .................................................. G01N 21/03
(52) U.S. Cl. ........................................ 250/343; 250/341.5
(58) Field of Search ................................... 250/343, 340, 250/341.1, 341.5, 339.06, 252.1; 356/440, 436

(56) References Cited

U.S. PATENT DOCUMENTS

| | | | |
|---|---|---|---|
| 4,630,684 | * | 12/1986 | Cenzori et al. ........................ 250/339 |
| 4,692,620 | * | 9/1987 | Rosenthal ............................. 250/343 |
| 5,241,178 | * | 8/1993 | Shields ................................. 250/339 |

OTHER PUBLICATIONS

Merberg, Evaluation of an Octane Analyzer, article reprinted from American Laboratory News, August 1996, 4 page pamphlet.

A Portable Near–Infrared Instrument for Quantitative Analysis of Octane in Gasoline, The Biotechnical Institute, The Second European Symposium on Near infrared (NIR) Spectroscopy Aspects of Industrial Use held at Kolding, Denmark, Aug. 30–Sep. 2, 1993, pp. 1–7.

Zeltex Inc., Zx–440 Near–Infrared Liquid Fuel Analyzer, 4 page brochure, 1996.

\* cited by examiner

*Primary Examiner*—Seungsook Ham
*Assistant Examiner*—Richard Hanig
(74) *Attorney, Agent, or Firm*—Rothwell, Figg, Ernst& Manbeck, P.C.

(57) ABSTRACT

A multiple-gain, hand-held, near-infrared grain analyzer analyzes, e.g., protein content of grain by infrared transmittance and interactance (transflectance) has at least two gain values. A first gain value is used when calibrating the analyzer with an empty analysis chamber (empty except for the presence of air), and a second, higher gain value is used when analyzing grain samples.

4 Claims, 6 Drawing Sheets

MULTIPLE GAIN PORTABLE NEAR-INFRARED ANALYZER

This application claims the benefit of Provisional No. 60/044,703 filed Apr. 18, 1997.

FIELD OF THE INVENTION

The invention relates to near-infrared analyzers which operate on the principle of transmittance and interactance (transflectance) and, in particular, to such analyzers which are portable.

BACKGROUND OF THE INVENTION

Near-infrared analyzers are relatively well-known and are used to analyze such diverse properties as the octane content of gasoline, the moisture content of cheese, and the oil/protein content of grain. They operate by passing near-infrared light into a sample that is to be tested and measuring the intensity of selected frequencies of the light that either passes through the sample or that is reflected back from the sample.

With relatively translucent materials such as gasoline, most of the light is able to pass through the sample. Therefore, relatively little amplification of the signal generated by the photodetector is needed. For such materials, the analyzer may be calibrated before testing of the sample simply by performing an analysis run on the empty test chamber. With other, relatively opaque materials such as grain or other food products, however, much of the light is absorbed or blocked by the material. Accordingly, when testing the material, it is necessary to amplify by greater amounts the photodetector signal to be able to extract the information used to analyze the content of the sample.

For portable or hand-held near-infrared analyzers configured to analyze grain or other relatively opaque samples, it has been customary to provide a sealed calibration standard having known parameters of interest for each type of grain or other material that is to be analyzed. The calibration standard is inserted into the analyzer first and a calibrating analysis run is performed on the standard. After the analyzer has been calibrated, the calibration standard is removed and the sample to be tested is inserted into the analyzer and analyzed.

Because the transmisivity of the calibration standard and the test sample are relatively the same, the photodetector signal generated when analyzing the test sample is not amplified any more than the photodetector signal generated when analyzing the calibration standard is. In other words, the analyzer operates at a single gain. This has been standard procedure for the past several years because it was believed that a dual gain portable analyzer was impractical. This is because noise in the signal—which tends to be present in the photodetector signal to a far greater extent in a hand-held unit than in a larger, better shielded laboratory or table-top unit—becomes amplified as well, and it had been believed that such noise amplification would make analysis of the signal unreliable.

Using calibration standards to calibrate the analyzer using the calibration standard is not ideal, however. This is because the standards tend to get soiled or smeared with debris as they are handled, and this can taint the calibration or otherwise degrade instrument performance. Additionally, the standards constitute extra equipment that can be lost and which needs to be carried with the analyzer. Accordingly, a portable hand-held, near-infrared analyzer for analyzing grain or other relatively opaque material that does not need calibrating standards to operate—i.e., one which can calibrate itself using an empty chamber—is desirable.

SUMMARY OF THE INVENTION

The present invention bucks the conventional wisdom and provides a near-infrared analyzer having two or more gain values associated with the photodetector signal. This allows the analyzer to be calibrated on an empty test chamber using a first, low gain value, and then the sample to be tested using a high gain value. Gain switching is effected by altering the resistance in the feedback path around the op-amp used to amplify the photodetector signal.

DESCRIPTION OF THE DRAWINGS

An embodiment of the invention will now be described in detail in conjunction with the following drawings, in which.

DETAILED DESCRIPTION of PREFERRED EMBODIMENTS

Figure 1:
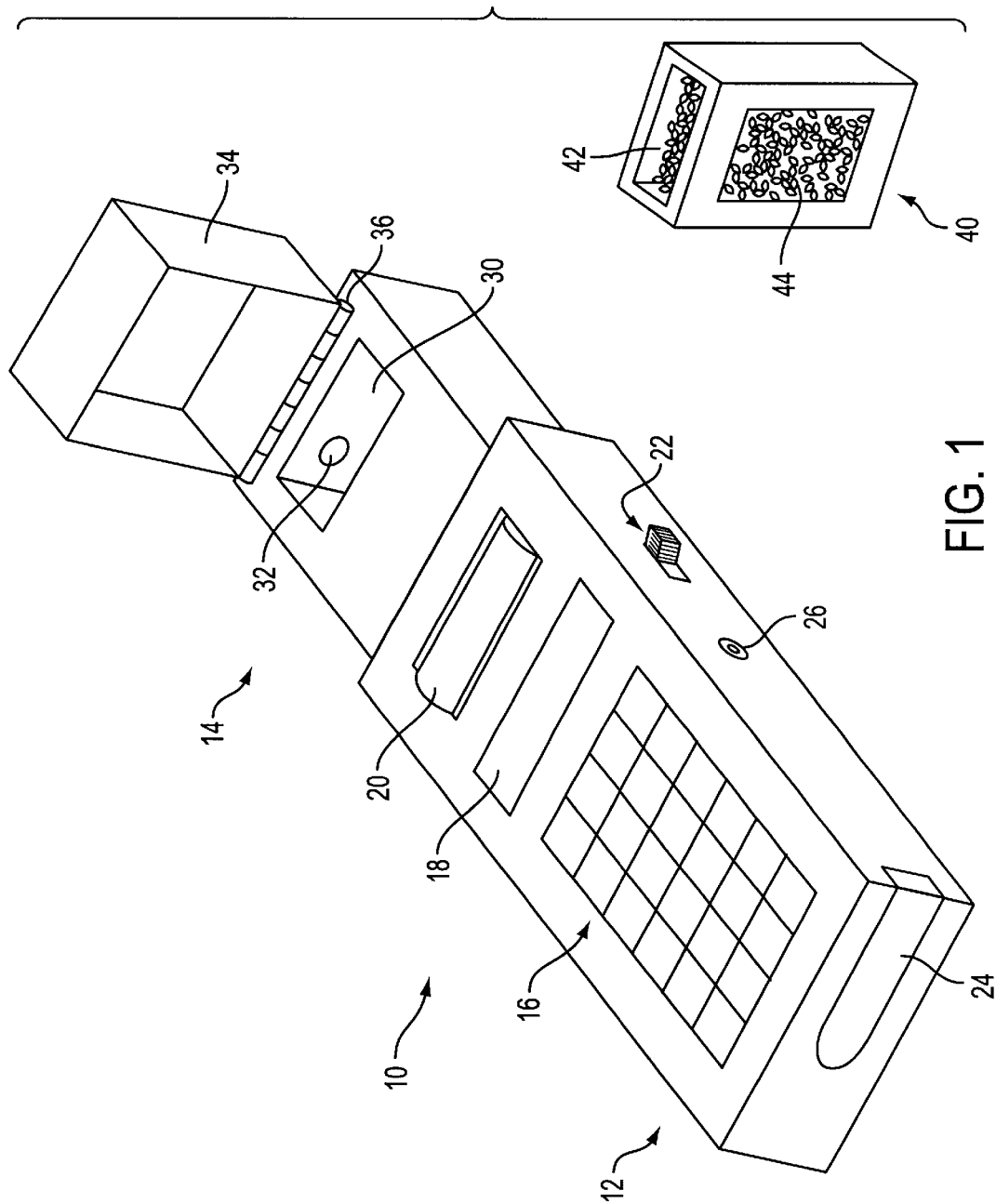
FIG. 1 is a perspective view showing a hand-held near-infared analyzer and a sample-containing cuvette.

A portable, hand-held, near-infrared analyzer 10 is shown in FIG. 1. The analyzer has a main, body portion 12 in which most of the electronics are housed and a sample-receiving portion 14. The body portion 12 has a keypad 16 that is used to control operation of the analyzer; a display window 18 that displays user prompts and results; and, optionally, a printer mechanism 20 such as a tape printer. The main, body portion 12 also has an on/off switch 22; a battery compartment 24; and an A/C adapter port 26.

The test chamber 30 constitutes a rectangular cavity in the sample-receiving portion 14. An array of near-infrared emitting diodes is housed in the sample-receiving portion 14, positioned to emit near-infrared light of various wavelengths from light port 32 located in one wall in the chamber. A photodetector (not visible in FIG. 1) is located directly opposite to the light port 32 in the wall of the test chamber 30 across from the light port 32. It will be noted that, for purposes explained below, the light port 32 (and hence the photodetector) is not centered laterally but, rather, is closer to one end of the test chamber than the other.

An opaque lid 34—preferably black—is pivotally attached to the sample-receiving portion 14, e.g., by means of hinge 36. The sample-receiving portion 14 and the lid 34 are constructed such that when the lid is closed, the test chamber 30 is entirely sealed from ambient light.

As further shown in FIG. 1, the sample of material, e.g., grain, is loaded into a generally rectangular cuvette 40. The cuvette has an upper opening 42, which may or may not be sealed, and a pair of transparent panels 44 on opposite sides which allow light emitted from the light port 32 to pass through the sample to the photodetector.

Figure 2:
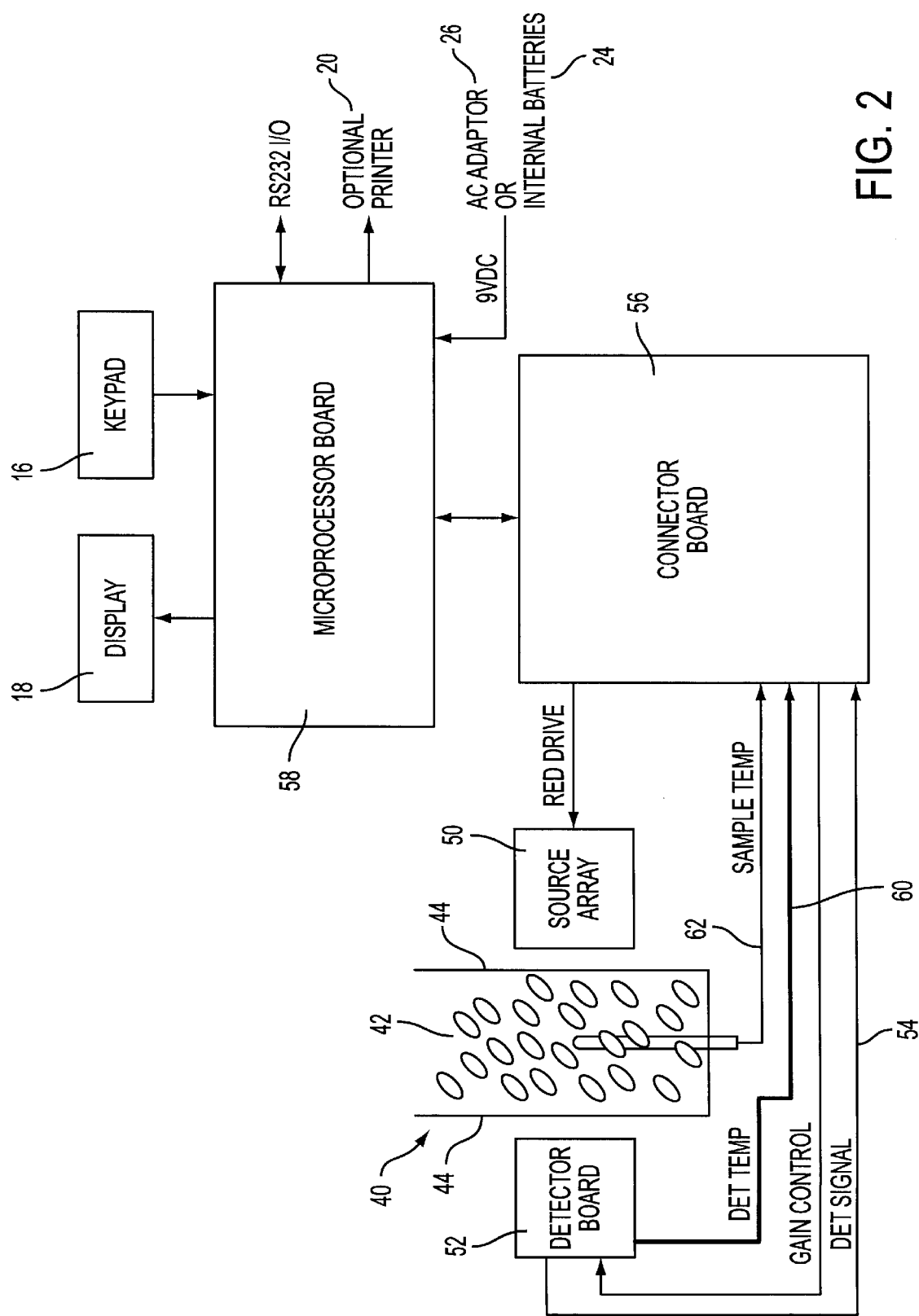
FIG. 2 is a schematic diagram showing the relationship between the electrical and optical components of the analyzer shown in FIG. 1.

The electronic components and test configuration of the near-infrared analyzer 10 are shown schematically in FIG. 2. The near-infrared emitting diodes are assembled together to form the source array 50, which illuminates the grain sample contained within the cuvette 40. The photodetector (not shown in FIG. 2), which is located on detector board 52, detects light passing through the sample and sends a signal along signal line 54, through connector board 56, and to a microprocessor (not shown) located on microprocessor board 58. In addition to the photodetector signal, the microprocessor receives signals indicating the temperature of the detector board and the sample; these signals are transmitted to the connector board along signal lines 60 and 62, respectively, and then to the microprocessor.

Figure 3:
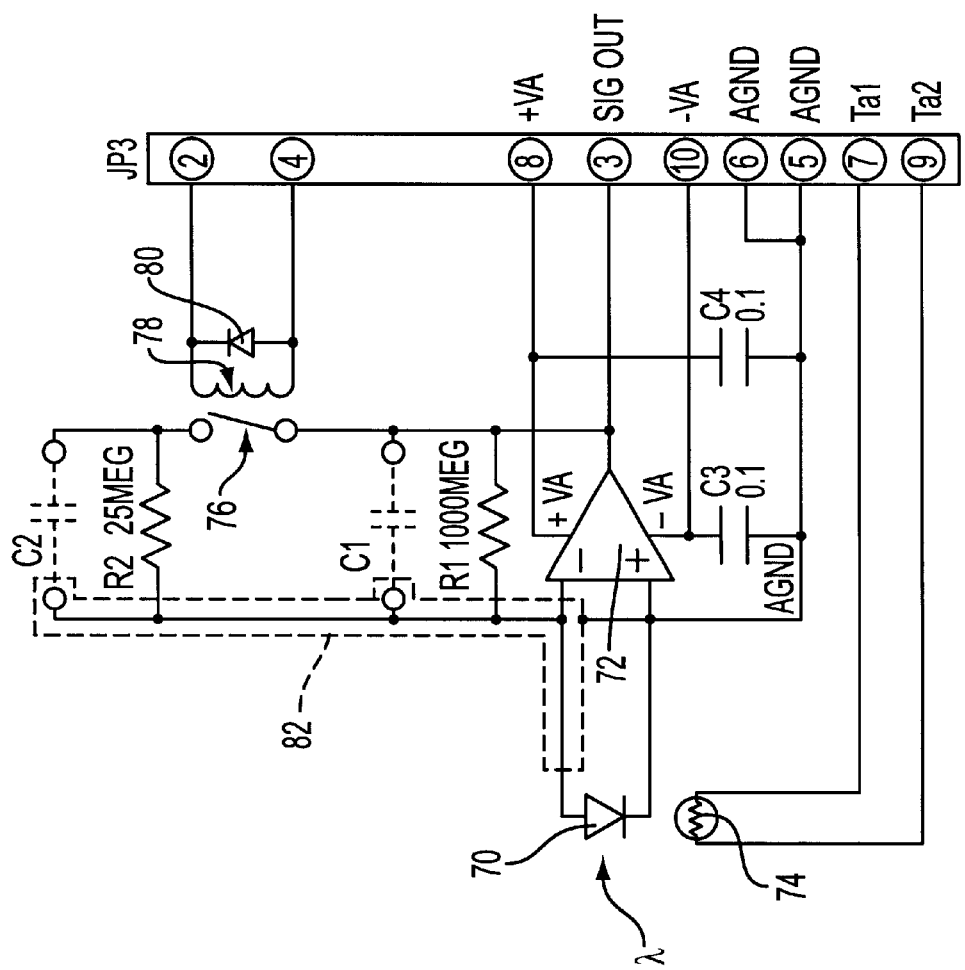
FIG. 3 is a schematic diagram showing components of the detector board shown in FIG. 2, which is configured to provide two different photodetector signal gain values.

Components of the detector board are shown in greater detail in FIG. 3. The photodetector 70 is a silicon photodiode, e.g., a Hamamatsu S1337 photodiode, the output current of which is proportional to the intensity of the light impinging on it. The photodetector is connected across pins 2 and 3 (negative and positive, respectively) of op-amp 72 which is, for example, a Harris 3160T op-amp. The output voltage of the op-amp (at pin 6) is measured by the microprocessor as the detector signal.

As noted above, the temperature of the photodetector (as well as the temperature of the sample) is measured and fed to the microprocessor. This is accomplished using thermistor 74 which is, for example, a Betatherm 10K3D409.

To this extent, the detector board components are as known in the art. With respect to the op-amp feedback path, however, it is modified to provide dual gain on the photodetector signal (op-amp output at pin 6). Specifically, the feedback path has a pair of resistors R1 and R2 arranged in parallel, with R1 having a significantly greater resistance than R2. For example, R1 is preferably 1,000 megohms and R2 is preferably 25 megohms.

Switch 76 is located between the resistors R1 and R2 and is provided by means of a reed relay. The switch is normally closed, in which case almost all the current in the feedback path flows through R2 (path of least resistance) and just a small amount flows through R1. When current flows through coil 78, on the other hand, the switch 76 is opened. This forces all the current to flow through R1 and the gain on the photodetector signal is increased by a factor of approximately 40 (1,000÷25). (Diode 80, arranged in parallel with the coil, protects the driver circuit from the voltage spike created when the field of the relay coil collapses.)

The circuitry also includes capacitors C1–C4, as well as a guard ring 82 surrounding high-impedance points on both sides of the circuit board. Capacitors C1 and C2 are integrating capacitors for noise reduction, if needed. Capacitors C3 and C4 are provided to bypass noise from the power lines $VA^+$ and $VA^-$ to ground.

Figure 4A:
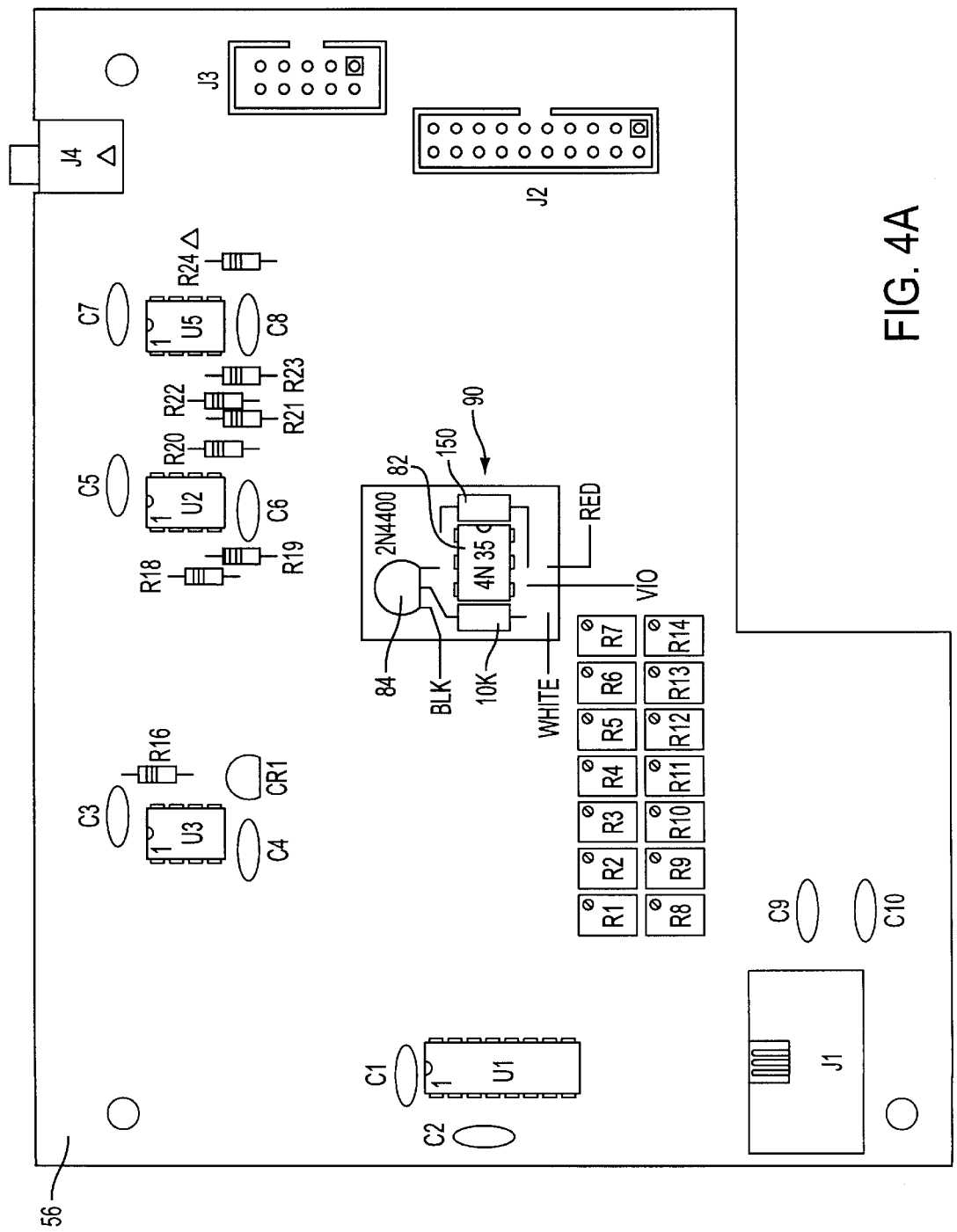
FIG. 4A is a schematic diagram showing components of the connector board shown in FIG. 2.
Figure 4B:
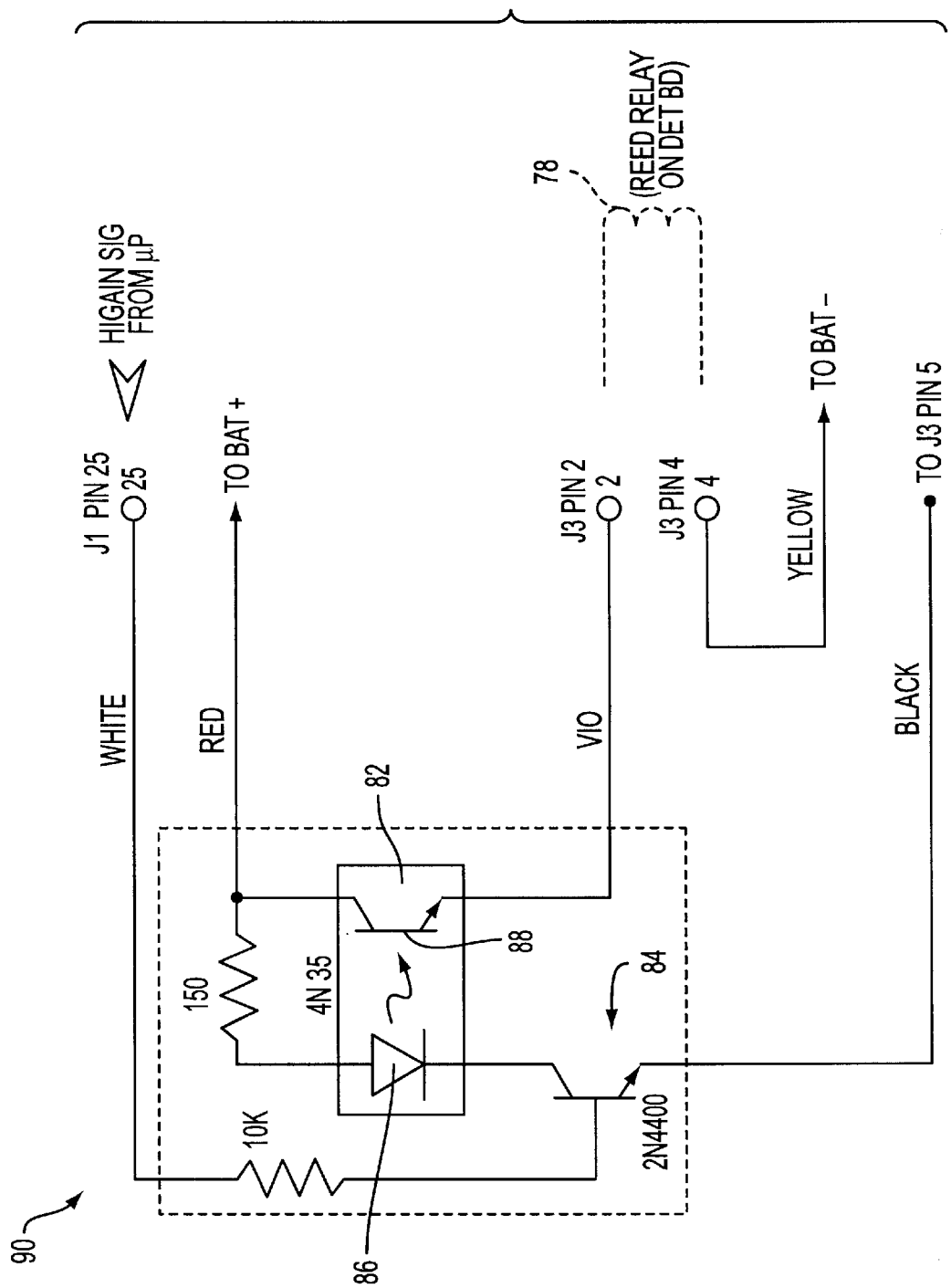
FIG. 4B is a more detailed schematic diagram showing components of the gain-switching circuit located on the connector board shown in FIGS. 2 and 4A.

The switch 76 is controlled by a gain-switching circuit 90, preferably located on the connector board 56 as shown in FIGS. 4A and 4B. The other components on the connector board are generally known in the field.

As shown in greater detail in FIG. 4B, the gain-switching circuit consists of a photocoupler 82, which is, for example, a 4N35 photocoupler, and a transistor 84, e.g., a 2N4400 transistor. When a high gain signal is issued by the microprocessor, the transistor 84 turns on, allowing current to flow through LED 86 which is embedded in the photocoupler chip 82. Light emitted by the LED 86 causes the embedded photoresistor 88 to turn on, thereby allowing current to flow to the coil 78 of the reed relay, which is indicated schematically in dashed lines. As noted above, this causes the switch 76 (FIG. 3) to open, thereby amplifying the photodetector signal by a gain factor of about 40.

In operation, the analyzer 10 is turned on and initialized with an empty test chamber 30. In other words, the lid 34 is closed with no sample in the test chamber, and a calibrating analysis of the empty test chamber is conducted.

After the analyzer has been calibrated, the microprocessor issues a high gain signal which causes the switch 76 to open, thereby increasing the photodetector signal gain. The cuvette 40 containing the sample is placed in the test chamber 30, the lid 34 is closed, and an analysis of the sample is performed using methods that are known in the art.

As is customary, two different sample analyses and their results are averaged. With prior art analyzers, in which the optics (light port 32 and photodetector 70) are laterally centered with respect to the length of the test chamber, it is necessary to discard the contents of the cuvette and fill it with another sample to avoid analyzing the exact same portions of the sample—albeit from opposite sides—which would skew the average value.

As noted above, however, the optics of the present analyzer are laterally shifted along the length of the test chamber; in other words, they are not centered. Therefore, rather than discarding the contents of the cuvette and refilling it, it is only necessary to rotate the cuvette by 180° and replace it in the test chamber. The sample is then analyzed once again—this time by passing the near-infrared light through a different portion of the sample—and the results are averaged.

Figure 5:
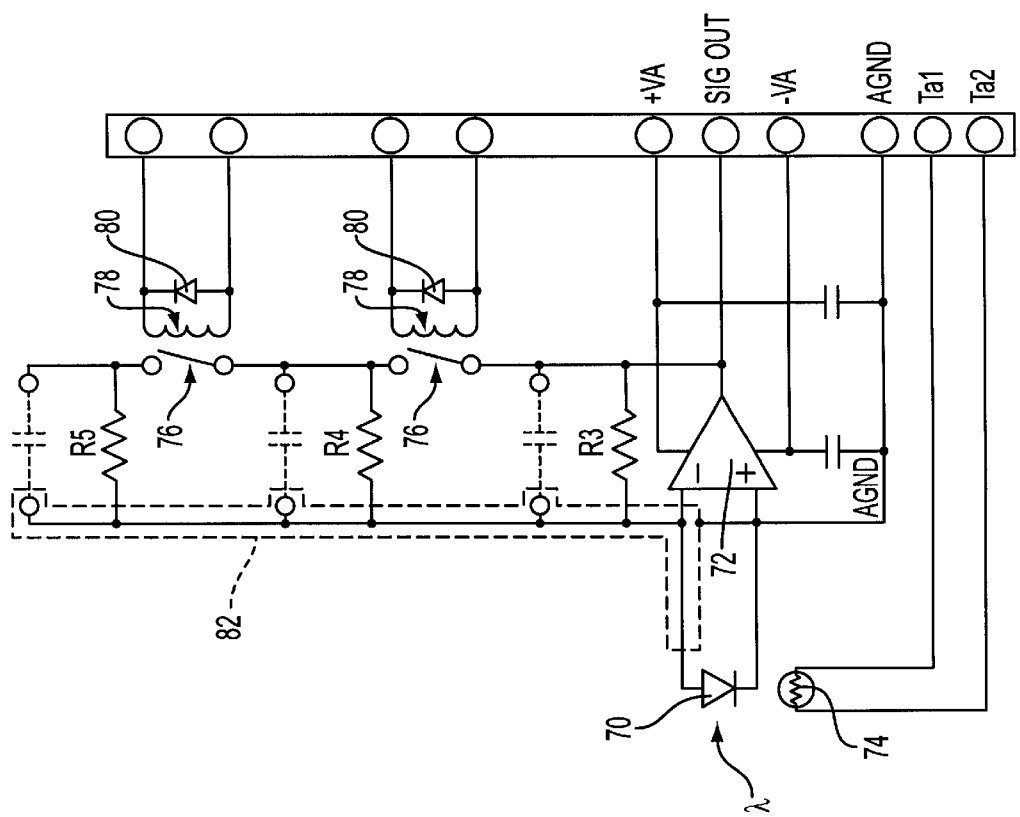
FIG. 5 is a schematic diagram showing components of a detector board that is configured to provide three different photodetector signal gain values.

Finally, it will be appreciated that the dual-gain principle of the present invention can be extended to provide three or even more different gain values. A configuration having three resistors R3, R4, and R5 in the feedback path and reed relay switches 76 between the three resistors is shown in FIG. 5. The switches are both normally closed, which provides a first gain value. By opening the switch between R4 and R5, then the switch between R3 and R4, two additional gain values are obtained.

Other embodiments are deemed to be within the scope of the following claims:

We claim:

1. A multiple gain, hand-held analyzer, said analyzer comprising:

an analyzer body configured to receive in a sample-receiving portion thereof of a sample to be analyzed;

a source which emits electromagnetic radiation at a desired wavelength, said source positioned with respect to said sample-receiving portion to emit radiation through a sample received in said sample-receiving portion;

an electromagnetic radiation receptor positioned such that electromagnetic radiation emitted by said source and passing through a sample received in said sample-receiving portion strikes said receptor, said receptor causing a first signal to be produced which is proportional to the intensity of electromagnetic radiation striking said receptor, said analyzer being configured such that said first signal is selectively amplified by a gain factor selected from a plurality of available gain factors to produce a second signal; and means for analyzing said second signal to determine a parameter of interest of a sample received in said sample-receiving portion;

wherein said analyzer is of a size and weight which permit said analyzer to be carried by hand and transported from one location to another for non-laboratory-bound field use;

wherein said analyzer is configured to be calibrated with said sample-receiving portion empty except for ambient air present therein, said first signal being amplified by a first gain factor when said analyzer is being calibrated and said first signal being amplified by a second gain factor when a sample is received in said sample-receiving portion and is being analyzed, said second gain factor being larger than said first gain factor; and wherein said second gain factor is of a magnitude sufficient to permit said analyzer to be used to analyze a sample of grain packed within a cuvette and disposed, in said cuvette, in said sample-receiving portion.

2. The analyzer of claim 1, wherein said second gain factor is approximately forty times said first gain factor.

3. The analyzer of claim 1 wherein said source emits near-infrared radiation.

4. A multiple gain, hand-held analyzer, said analyzer comprising:

an analyzer body configured to receive in a sample-receiving portion thereof a sample to be analyzed;

a source which emits electromagnetic radiation at a desired wavelength, said source positioned with respect to said sample-receiving portion to emit radiation through a sample received in said sample-receiving portion;

an electromagnetic radiation receptor positioned such that electromagnetic radiation emitted by said source and passing through a sample received in said sample-receiving portion strikes said receptor, said receptor causing a first signal to be produced which is proportional to the intensity of electromagnetic radiation striking said receptor, said analyzer being configured such that said first signal is selectively amplified by a gain factor selected from a plurality of available gain factors to produce a second signal; and means for analyzing said second signal to determine a parameter of interest of a sample received in said sample-receiving portion;

wherein said analyzer is of a size and weight which permit said analyzer to be carried by hand and transported from one location to another for non-laboratory-bound field use;

wherein said analyzer is configured to be calibrated with said sample-receiving portion empty except for ambient air present therein, said first signal being amplified by a first gain factor when said analyzer is being calibrated and said first signal being amplified by a second gain factor when a sample is received in said sample-receiving portion and is being analyzed, said second gain factor being larger than said first gain factor;

wherein said sample-receiving portion is configured with a least one axis of symmetry such that a cuvette, used to hold a sample to be analyzed and configured to fit precisely within said sample-receiving portion, can fit within said sample-receiving portion with more than one orientation; and wherein said source and said receptor are offset relative to said axis of symmetry whereby electromagnetic radiation can be caused to pass through multiple portions of a sample to be analyzed by positioning said cuvette in said sample-receiving portion with two or more orientations.

* * * * *